(12) United States Patent  (10) Patent No.: US 8,355,133 B2
Dultz et al.  (45) Date of Patent: Jan. 15, 2013

(54) BIOLOGICAL TESTING WITH SAWTOOTH-SHAPED PRISMS

(75) Inventors: Shane C. Dultz, Westlake Village, CA (US); David Ralin, South Pasadena, CA (US)

(73) Assignee: Maven Technologies, LLC, Monrovia, CA (US)

( * ) Notice: Subject to any disclaimer, the term of this patent is extended or adjusted under 35 U.S.C. 154(b) by 396 days.

(21) Appl. No.: 12/650,327

(22) Filed: Dec. 30, 2009

(65) Prior Publication Data

US 2011/0157693 A1 Jun. 30, 2011

(51) Int. Cl.
*G01N 21/55* (2006.01)
(52) U.S. Cl. .................................................. 356/445
(58) Field of Classification Search .................. None
See application file for complete search history.

(56) References Cited

U.S. PATENT DOCUMENTS

| | | |
|---|---|---|
| 1,637,141 A | 7/1927 | Cooper |
| 3,177,759 A | 4/1965 | Wilkes, Jr. et al. |
| 3,279,307 A | 10/1966 | Wilkes, Jr. et al. |
| 3,858,616 A | 1/1975 | Thiery et al. |
| 4,146,365 A | 3/1979 | Kay et al. |
| 4,238,565 A | 12/1980 | Hornby et al. |
| 4,256,834 A | 3/1981 | Zuk et al. |
| 4,508,832 A | 4/1985 | Carter et al. |
| 5,164,589 A | 11/1992 | Sjoedin |
| 5,225,164 A | 7/1993 | Astle |
| 5,229,833 A | 7/1993 | Stewart |
| 5,234,769 A | 8/1993 | Shevlin |
| 5,255,075 A | 10/1993 | Cush |
| 5,313,264 A | 5/1994 | Ivarsson et al. |
| 5,341,215 A | 8/1994 | Seher |
| 5,437,840 A | 8/1995 | King et al. |
| 5,446,534 A | 8/1995 | Goldman |
| 5,483,346 A | 1/1996 | Butzer |
| 5,485,277 A | 1/1996 | Foster |
| 5,491,097 A | 2/1996 | Ribi et al. |
| 5,491,556 A | 2/1996 | Stewart et al. |
| 5,573,956 A | 11/1996 | Hanning |
| 5,593,130 A | 1/1997 | Hansson et al. |

(Continued)

FOREIGN PATENT DOCUMENTS

AU 742417 2/2000

(Continued)

OTHER PUBLICATIONS

International Search Report, issued Mar. 4, 2011, by the European Patent Office in connection with International Application No. PCT/US2010/059854.

(Continued)

*Primary Examiner* — Gregory J Toatley
*Assistant Examiner* — Amanda Merlino
(74) *Attorney, Agent, or Firm* — Haynes and Boone, LLP

(57) ABSTRACT

In one embodiment, an apparatus is provided for testing for the presence of analytes in a sample. The apparatus comprises a source of light directed at the bottom surface of a substrate to achieve total internal reflection and to generate an evanescent field. An array of capture elements is immobilized on the top surface of the substrate. The bottom surface of the substrate is configured as a sawtooth (in cross section), the "teeth" aligned with the rows or the columns in the array. The outer faces of the sawtooth "prisms" are non-parallel to the substrate top surface, and specific requirements are imposed on the prism light-entrance face, and the substrate thickness and refractive index.

25 Claims, 7 Drawing Sheets

U.S. PATENT DOCUMENTS

| | | |
|---|---|---|
| 5,633,724 A | 5/1997 | King et al. |
| 5,641,640 A | 6/1997 | Hanning |
| RE35,716 E | 1/1998 | Stapleton et al. |
| 5,738,825 A | 4/1998 | Rudigier et al. |
| 5,753,518 A | 5/1998 | Karlsson |
| 5,796,858 A | 8/1998 | Zhou et al. |
| 5,813,439 A | 9/1998 | Herrero et al. |
| 5,856,873 A | 1/1999 | Naya et al. |
| 5,922,594 A | 7/1999 | Loefas |
| 5,922,604 A | 7/1999 | Stapleton et al. |
| 5,955,729 A | 9/1999 | Nelson et al. |
| 5,965,456 A | 10/1999 | Malmqvist et al. |
| 5,972,612 A | 10/1999 | Malmqvist et al. |
| 6,008,010 A | 12/1999 | Greenberger et al. |
| 6,008,893 A | 12/1999 | Roos et al. |
| 6,026,053 A | 2/2000 | Satorius |
| 6,045,996 A | 4/2000 | Cronin et al. |
| 6,065,501 A | 5/2000 | Feret et al. |
| 6,127,183 A | 10/2000 | Ivarsson et al. |
| 6,140,044 A | 10/2000 | Bessemer et al. |
| 6,143,513 A | 11/2000 | Loefas |
| 6,143,574 A | 11/2000 | Karlsson et al. |
| 6,197,595 B1 | 3/2001 | Anderson et al. |
| 6,200,814 B1 | 3/2001 | Malmqvist et al. |
| 6,207,381 B1 | 3/2001 | Larsson et al. |
| 6,253,793 B1 | 7/2001 | Dupoiron et al. |
| 6,277,330 B1 | 8/2001 | Liu et al. |
| 6,289,286 B1 | 9/2001 | Andersson et al. |
| 6,354,333 B1 | 3/2002 | Dupoiron et al. |
| 6,355,429 B1 | 3/2002 | Nygren et al. |
| 6,415,825 B1 | 7/2002 | Dupoiron et al. |
| 6,475,809 B1 | 11/2002 | Wagner et al. |
| 6,493,097 B1 | 12/2002 | Ivarsson |
| 6,503,760 B2 | 1/2003 | Malmqvist et al. |
| D472,644 S | 4/2003 | Dawson et al. |
| 6,549,011 B2 | 4/2003 | Flatt |
| 6,589,798 B1 | 7/2003 | Loefas |
| 6,594,011 B1 | 7/2003 | Kempen |
| D480,149 S | 9/2003 | Dawson et al. |
| 6,698,454 B2 | 3/2004 | Sjoelander et al. |
| 6,710,870 B1 | 3/2004 | Marowsky et al. |
| 6,714,303 B2 | 3/2004 | Ivarsson |
| 6,806,051 B2 | 10/2004 | Ellson |
| 6,810,286 B2 | 10/2004 | Donovan et al. |
| 6,833,920 B2 | 12/2004 | Rassman et al. |
| 6,859,280 B2 | 2/2005 | Kempen |
| 6,882,420 B2 | 4/2005 | Rassman et al. |
| 6,981,526 B2 | 1/2006 | Glejbol et al. |
| 7,045,287 B2 | 5/2006 | Smith et al. |
| 7,193,711 B2 | 3/2007 | Rassman et al. |
| 7,195,872 B2 | 3/2007 | Agrawal et al. |
| 2002/0019019 A1 | 2/2002 | Hamalainen et al. |
| 2002/0154311 A1 | 10/2002 | Ivarsson |
| 2002/0182717 A1 | 12/2002 | Karlsson |
| 2003/0022388 A1 | 1/2003 | Roos et al. |
| 2003/0067612 A1 | 4/2003 | Ivarsson |
| 2003/0112432 A1 | 6/2003 | Yguerabide et al. |
| 2003/0148401 A1 | 8/2003 | Agrawal et al. |
| 2003/0205681 A1 | 11/2003 | Modlin |
| 2003/0232384 A1 | 12/2003 | Kocher et al. |
| 2004/0002167 A1 | 1/2004 | Andersson et al. |
| 2004/0012676 A1 | 1/2004 | Weiner et al. |
| 2004/0023247 A1 | 2/2004 | Xu et al. |
| 2004/0030504 A1 | 2/2004 | Helt et al. |
| 2004/0038268 A1 | 2/2004 | Pirrung et al. |
| 2005/0017191 A1 | 1/2005 | Montagu et al. |
| 2005/0148063 A1 | 7/2005 | Cracauer et al. |
| 2006/0263874 A1 | 11/2006 | Kunuki et al. |
| 2009/0237670 A1* | 9/2009 | Osborne et al. ............ 356/445 |

FOREIGN PATENT DOCUMENTS

| | | |
|---|---|---|
| EP | 0257955 | 3/1988 |
| EP | 2116839 | 11/2009 |
| JP | 11304693 | 11/1999 |
| WO | WO 8911057 | 11/1989 |
| WO | WO 9100467 | 1/1991 |
| WO | WO 9522754 | 8/1995 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

Written Opinion of the International Searching Authority, issued Mar. 4, 2011, 2008, by the European Patent Office in connection with International Application No. PCT/US2010/059854.

U.S. Appl. No. 11/677,674, Dultz et al.

U.S. Appl. No. 11/748,023, Dultz et al.

U.S. Appl. No. 11/696,369, Dultz.

U.S. Appl. No. 11/752,056, Dultz.

U.S. Appl. No. 12/125,685, Dultz.

U.S. Appl. No. 12/125,735, Dultz et al.

Tadashi Saitoh, et al."Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

"Handbook of Optics", Michael Bass Editor in Chief, by The Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices—The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry a User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

Ch Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay at Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elsevier Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

Willems, Goerge M., et al., Adsorption and Conversion of Prothrombin on a Rotating Disc, Blood, Jul. 15, 1993, vol. 82, No. 2, pp. 497-504.

* cited by examiner

BIOLOGICAL TESTING WITH SAWTOOTH-SHAPED PRISMS

CROSS-REFERENCE TO RELATED APPLICATIONS

This application is related to pending U.S. application Ser. No. 12/125,735, filed May 22, 2008, the contents of which are incorporated by reference herein for all purposes.

FIELD OF THE INVENTION

This invention relates to determining the presence of analytes in a sample and more specifically to apparatus and methods which employ an array of capture elements immobilized on a substrate which respond when exposed to a sample to provide patterns of binding events.

BACKGROUND

U.S. Pat. No. 6,594,011 issued Jul. 15, 2003 describes an apparatus which employs a substrate with an array of capture elements immobilized on the top surface of the substrate. When the array is exposed to a fluid sample, patterns of binding events occur in the array depending on the analytes present in the sample. The patterns of binding events are captured by directing a beam of polarized light through a prism abutting the bottom surface of the substrate. The beam is directed at an angle to obtain total internal reflection (TIR) and to generate an evanescent field in the plane of the array. The pattern of binding events is imposed on a detection device such as a CCD camera and compared with a stored image of the array captured prior to exposure to the sample. The localized changes in the intensities of reflected light and the locations of those changes in the array are representative of the various analytes present in the sample.

SUMMARY

In accordance with the principles of this invention, the bottom surface of a substrate which either has or is intended to have an array of capture elements immobilized on its top surface, is configured to have a plurality of prisms which have a sawtooth cross-sectional shape. The prisms conveniently align as wedges parallel to either rows or columns of wells in the plate, and are comprised of outer planes (e.g., entrance and exit faces) that are non-parallel to the top surface of the substrate. Further, the incident prism face (aperture) for the light has to be sufficiently large and the substrate to which the prisms are coupled has to be sufficiently thick to limit divergence of the incident beam and to ensure the light enters and exits the prism film in a way which minimizes effects on beam polarization, respectively.

The size of the sawtooth prism pattern is important because the design allows for the possibility of imaging a surface up to a millimeter past the sawtooth structure which requires minimizing diffraction effects. The structural design of the present disclosure is thus distinguished from a diffraction grating which splits and diffracts light into several beams traveling in different directions based on the wavelength. For a diffraction grating, the grating spacing (pitch), and angles of the incident and diffracted beams follow what is known as the grating equation and diffraction is required to achieve the desired effect. Although diffraction can never be eliminated, the effects may be reduced to acceptable levels by adhering to the geometric constraints discussed below.

The sawtooth prism pattern disclosed herein can be formed in a film which can be attached to the substrate bottom surface in the absence of an index matching fluid, or the bottom surface may have an integral sawtooth bottom configuration in another embodiment. The "substrate" herein should be transparent to the light used for detection and have sufficiently low surface roughness at the top surface where total internal reflection (TIR) occurs. This substrate can be comprised of a transparent material, such as glass or plastic, and can be integral to or a part of the entire disposable. Typically, the substrate will either have the dimensions of a microscope slide or have a length and width close to the glass and plastic substrates used in glass bottom multiwell plates. In accordance with ANSI/SBS standards for multiwell plates, typical configurations for the disposables are slides with wells (9 mm center-to-center spacing for 96 well plates and 4.5 mm spacing for 384-well plates), and glass bottom 96-well and 384-well plates. It is also possible that the substrate can be a part of a microfluidic disposable device with precisely patterned channels on the top surface of the substrate and a prism film attached to the bottom surface.

DETAILED DESCRIPTION

Figure 1:
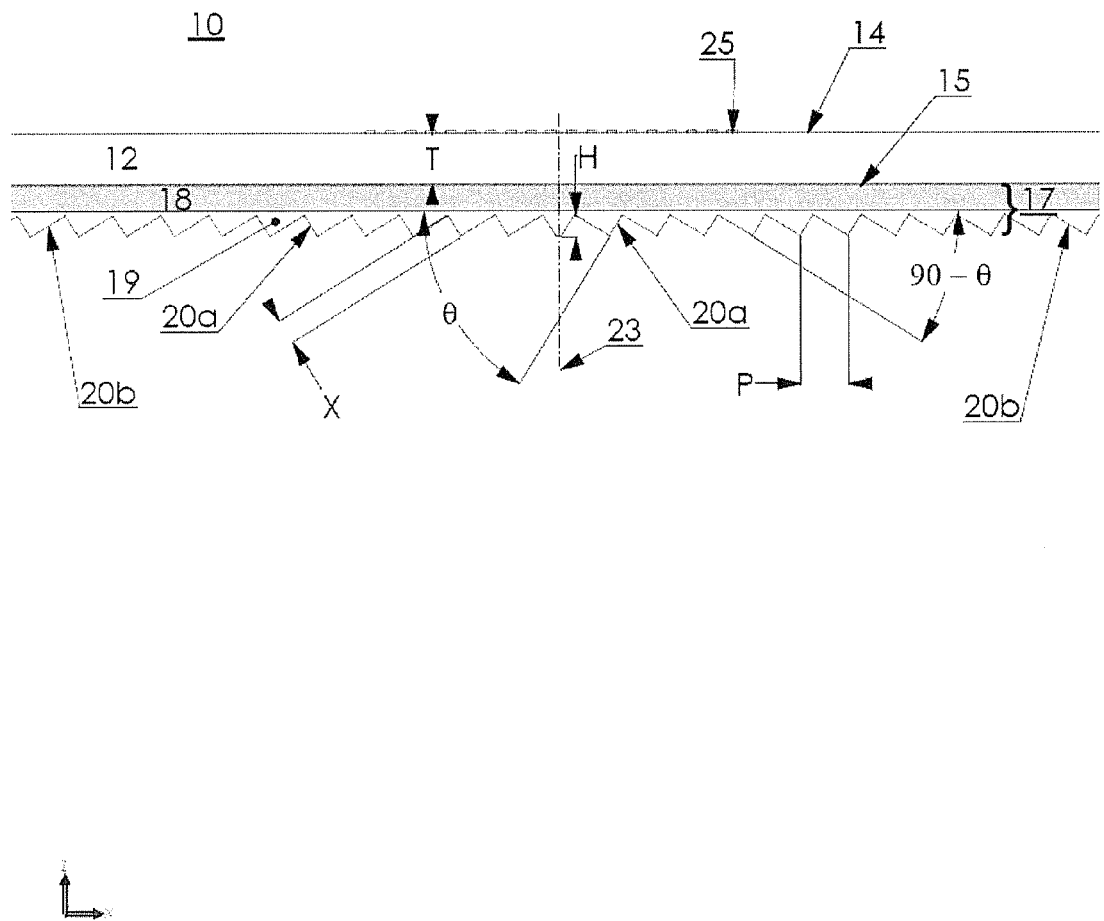
FIGS. 1 and 2 are schematic side views of substrates with a sawtooth-shaped bottom surface in accordance with the principles of this disclosure.

Prior to describing embodiments of the present disclosure in greater detail, the following definition is provided for use throughout the present document.

Sawtooth: A jagged or zigzag repeating pattern, outline, or course. In one embodiment, the cross-section of each prism is, illustratively, a right triangle sawtooth.

The present disclosure relates to apparatus and methods for determining the occurrence of binding events between different ligands in an array of ligands immobilized on the top surface of a transparent substrate and analytes in a sample to which the array is exposed. In one embodiment of the present disclosure, the bottom surface of the substrate has a sawtooth cross-sectional geometry with each prism (e.g., a right triangle prism) parallel with the rows or with the columns of the array of ligands. Each prism may extend across the entire substrate (a few inches for a 96-well plate for example) or be any length less than the substrate dimension. For example, each prism may extend only across a single well (underneath a 96-well plate) so that each prism is 7.5 mm long, allowing for flat regions between wells that can be used for light intensity calibration. The "sawtooth" geometry is useful for any related technology which directs light into the bottom surface of a substrate which has, or is intended to have on the top surface thereof an array of capture elements (ligands) to test for the presence of analytes in a sample.

Although the cross section geometry of a sawtooth is easily visualized as is the alignment of "tooth" wedges with a row (or column) of an array, there are some constraints on the geometry. Specifically, it has been realized that once the area of an array is determined (by choice), the thickness of the substrate, the index of refraction of the substrate and the entrance and exit faces of the wedges are constrained. If the apparatus further includes multiple test sites, the spacing between cells also becomes a constraint.

The sawtooth is formed with outer faces that are non-parallel to the plane of the top surface of the substrate but which form right angles between adjacent faces in one embodiment. In other embodiments, the sawtooth may be formed entirely with outer faces that are non-parallel to the plane of the substrate top surface and which do not form right angles between adjacent faces. The second embodiment is useful for disposable designs where the incoming light would not be incident perpendicular to the first surface of each prism.

It is noted that the disclosure herein is described illustratively with respect to the apparatus described in the above-mentioned U.S. Pat. No. 6,594,011 but may be used with various apparatus using light from beneath a substrate to image patterns of binding events, for example via spatially-distributed polarization changes or other techniques.

The following disclosure presents equations and graphs relating the ranges of parameter choices once a field of view (FOV) is decided. In an experimental apparatus the sawtooth microprism film structure was defined in a two-component film separate from the substrate. The film consisted of a plastic material (COC) bound to a UV cured polymer formed into the shape of microprisms and an adhesive was used to adhere the film to the bottom surface of the substrate. No fluid interface was necessary and the sawtooth microprisms were laminated directly on the substrate bottom surface. In the production of high volume prism film disposable structures, care must be taken to avoid introducing stress birefringence in the prism films themselves. For example, in a lamination process, this is achieved by controlling the pressure between the roller and the substrates and the tension in the unwinding film. The most important specification is not the total birefringence but the birefringence variability in the prism film. A constant but uniform birefringence in the film can be compensated for with an appropriate optical coating on the top surface of the substrate whereas too much birefringence variability will impact the repeatability of an optical measurement made through the underside of such a disposable.

A prism film structure, in one embodiment, may be comprised of four different materials which create the stack structure: the prisms (UV polymer), the plastic substrate (COC), the adhesive, and the glass. In order to have a complete equation for the maximum field of view, we need two (2) parameters for every material in the stack. An approximation is to treat the prism film structure as being made of a single material so that the field of view can be written in terms of the overall thickness and average refractive index only. This approximation is valid as long as effort is made to index match all four materials as closely as possible. If we define the field of view as measured along the direction of light propagation only and let T stand for thickness of the substrate and n stand for the index of refraction of the substrate, the following constraints exist for the maximum field of view (FOV):

$$FOV \leq 2T \tan\left[\sin^{-1}\left(\frac{1.344}{n}\right)\right]$$ (Equation 1)

and $$FOV \leq 9 - 2T \tan\left[\sin^{-1}\left(\frac{1.344}{n}\right)\right]$$

The first constraint ensures that reflected light does not exit prisms of the wrong orientation and the second constraint ensures that the entry and exit portions of the prism field do not extend beyond the well-well spacing of 9 mm. Accordingly, an allowable combination of FOV and substrate thickness must fit within the triangular region in the graph shown in FIG. 7. The value, $1.344 = n \sin(\theta)$, is determined by optically modeling the optimum angle of incidence inside the substrate. This number is dependent on the refractive index of the sample being measured.

Figure 7:
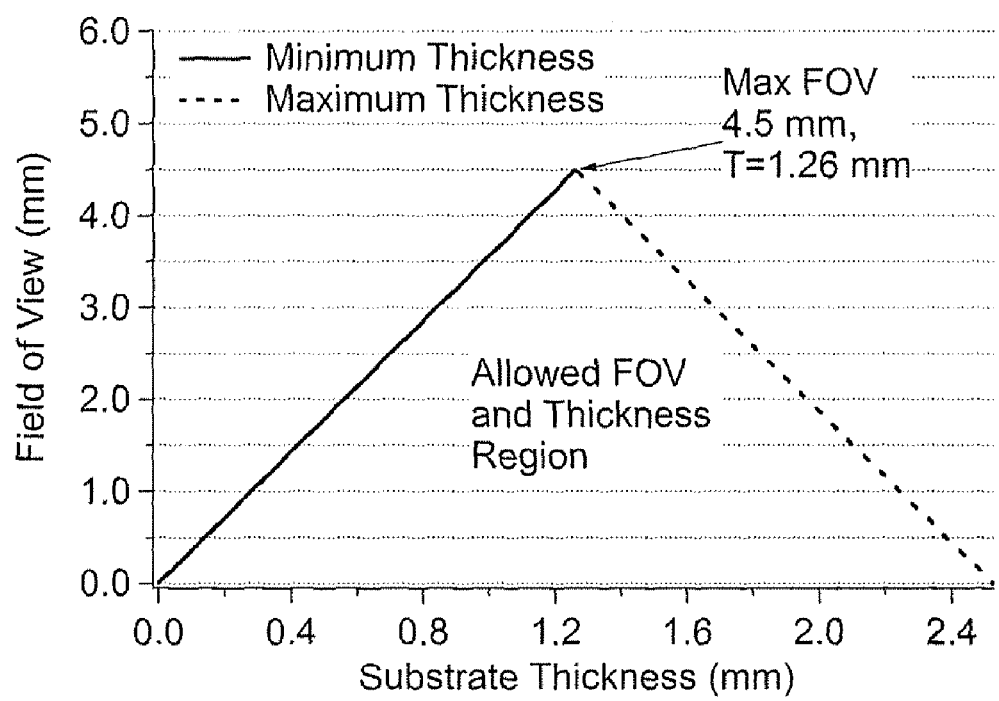
FIG. 7 is a graph illustrating field of view versus substrate thickness.

One way to read the graph of FIG. 7 is to specify a desired FOV for the measurement and determine the range of substrate thicknesses allowable for that field of view. For example, for a 4.5 mm FOV, there is only one possible substrate thickness, 1.26 mm. However, a 4.0 mm FOV is achieved for any substrate thickness between 1.12 mm and 1.4 mm.

Referring now to FIG. 1, a schematic cross-section of apparatus 10 is illustrated in accordance with an embodiment of the present disclosure. The apparatus 10 comprises a glass substrate 12 having a thickness T and parallel top and bottom surfaces 14 and 15, respectively. A prism film 17 is attached to bottom surface 15 of the substrate 12. In one example, the prism film 17 comprises a planar layer 18 formed of Cyclic Olefin Copolymer (COC) and a sawtooth layer 19 formed of UV-cured acrylic ester. It is noted that other materials can be used for the prism film (for either the planar layer or the sawtooth layer).

The sawtooth prisms can be seen in layer 19 to comprise outer faces (or facets) which are non-parallel to the substrate top (or bottom) surface. In one embodiment, the sawtooth prisms in layer 19 consist of only outer faces (or facets), which are non-parallel to the substrate top/bottom surfaces 14, 15. A prism facet 20a has a dimension X and the sawtooth layer 19 has a thickness H and a period P as indicated in FIG. 1. The prism facets 20a are formed at an angle θ with respect to top/bottom surfaces 14, 15. If the incoming light beam is incident normal to prism facets 20a, 0 will also be the angle of incidence and the light will exit normal to prism facets 20a on the other side of broken line 23 which is transversely centered about each well (not shown in FIG. 1). Prism facets 20b are not meant to be surfaces for light entry and exit. For example, if the substrate thickness is too thin, light will exit those faces and refract so strongly that the light will re-enter the neighboring 20a faces without exiting the prism film structure when θ=58.3°, which is the case in FIG. 1. Light transmission through the entire disposable is maximized when the faces 20a and 20b make a right angle for a perfectly collimated system.

A ligand (protein) array 25 is provided at the top surface 14 of substrate 12. In some embodiments, the ligand array may extend across the entire surface of the substrate. In other embodiment, the same array is repeated at the bottom of every well of a glass-bottom, 96-well plate where the spatial extent of the ligand array may cover 7.5 mm×4.5 mm at the center of each well. For any complete structure with a fixed well-to-well spacing, the alternating sawtooth pattern period must scale directly with that well spacing.

Figure 2:
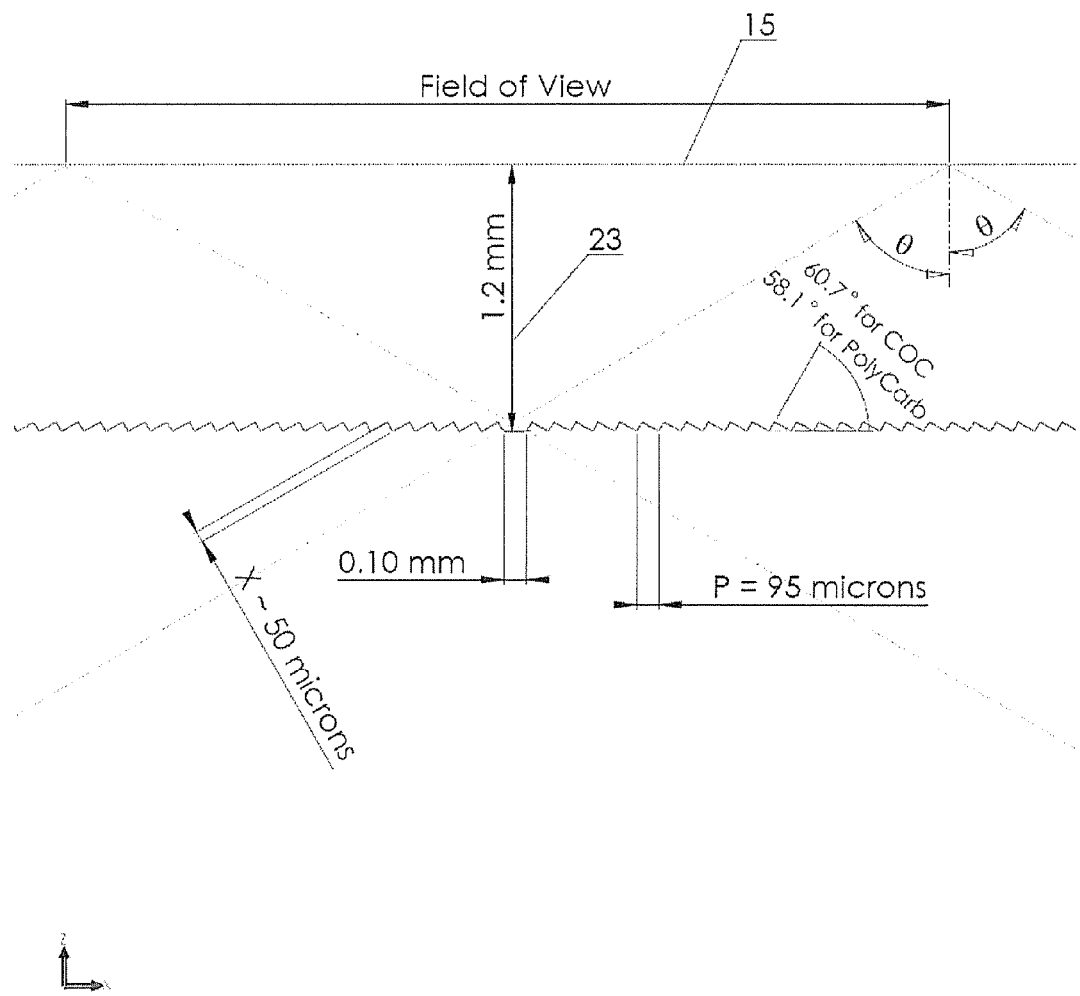

FIG. 2 is an enlarged schematic sideview of prisms which are part of a single material structure (i.e., an integral injection molded part) where, in one example, X=0.05 mm and P=0.095 mm. As noted hereinbefore, the prism geometry can be formed directly on the bottom surface of the substrate and FIG. 2 illustrates such a simplified apparatus. In the case of 96-well plates, in order to get light in and out of every well with the light perpendicular to the entry and exit faces of the sawtooth structure, the thickness of the entire bottom structure should be close to 1.2 mm in order to maximize the field of view of the ligand arrays. This thickness constraint is directly proportional to the well-to-well spacing so that the same geometry with 384-well plates would require a thickness of 0.6 mm in order to maximize the field of view. The constraint also assumes that light is allowed to enter and exit each well of the plate individually and that the field of view is always centered within the well.

The sawtooth-shaped prism configuration for the substrate bottom surface has the attractive characteristic of virtually eliminating multiple reflections of an incident light beam. The reason for this is that the sawtooth does not have faces (or facets) parallel to the plane of the micro array of ligands (i.e., the substrate top surface).

Diffraction is also an important constraint on the sawtooth geometry. The light entering each of the (sawtooth) prisms will diverge due to diffraction. It is preferable that the light diverges no more than about 0.5 degrees before striking the (protein) array. To limit the divergence, the shorter dimension (X) of the entry face of any prism is determined by:

$$X \geq \frac{\lambda}{\sin\varphi}, \quad \text{(Equation 2)}$$

where $\varphi$ is the divergence half angle of the beam.

If $\varphi \leq 0.5°$, then $X \geq 50$ microns at a wavelength of about 450 nm. As a result, the pitch, $$P = \frac{X}{\cos\theta},$$

where $\theta$ is the angle of incidence of the incoming light with respect to the plane of the microarray, would have to be greater than 95 microns in this example. For a test apparatus with prism material having an index of refraction n of 1.58, the ideal angle of incidence (AOI) is 58.3 degrees as shown in FIG. 1. The sawtooth prism film structure can be made with smaller prism pitches because there are no flat planar faces between neighboring prisms. From a diffraction perspective it is preferable to have the prisms as large as possible with a pitch greater than 95 microns for a 58.3 degrees AOI.

Figure 3:
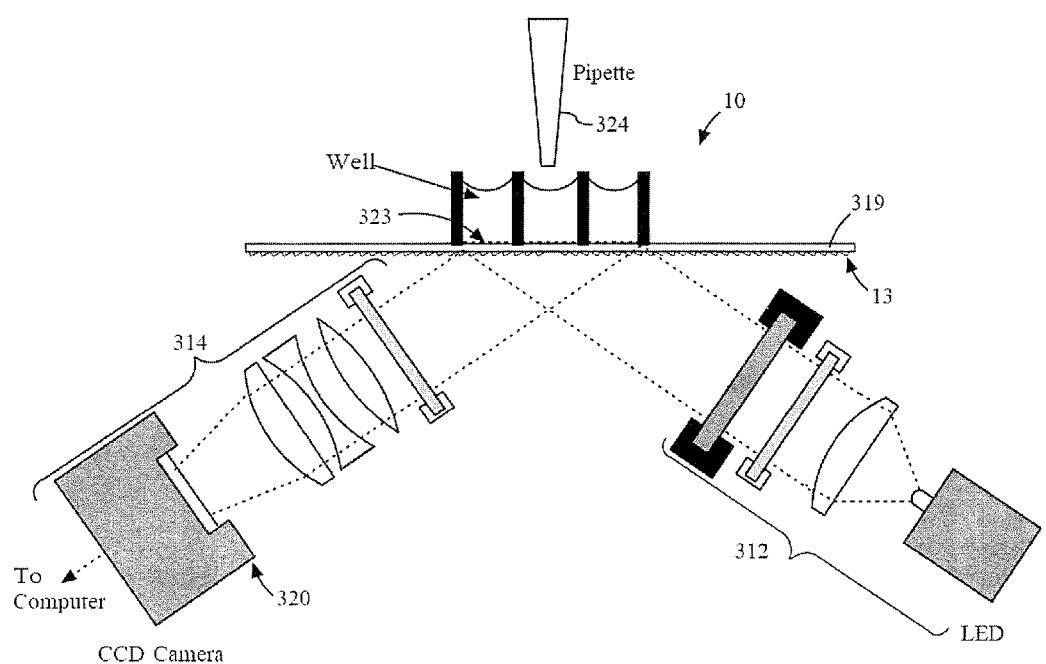
FIG. 3 is a block diagram of an optical system useful with a substrate configured as shown in FIGS. 1 and 2.

FIG. 3 shows an illustrative optical system for use with a substrate with a sawtooth bottom surface in accordance with an embodiment of the present disclosure. Components of the optical system, such as an optical light subsystem and an optical sensing subsystem, are described in U.S. Pat. No. 6,594,011 issued Jul. 15, 2003, which has been previously incorporated by reference for all purposes. Suffice it to say that light from optical subsystem 312 is totally internally reflected from the bottom surface of substrate 319. Optical sensing subsystem 314 including a CCD camera 320 is operative to capture the reflected image of any binding events between ligands in a microarray on the top surface 323 of substrate 319 and analytes in a sample introduced, for example, by pipette 324 into one of the illustrative three wells shown.

In one experimental apparatus, a "disposable" device as shown in FIG. 1, was comprised of sawtooth prisms made of UV-cured acrylic ester on a COC plastic planar layer backing about 80 microns thick. The sawtooth prisms and planar backing were coupled to a substrate comprised of a Schott D-263 microscope slide with optical silicon dioxide coatings 2 nm, 4 nm and 6 nm thick. Neighboring faces of the sawtooth were 90 degrees to one another with each tooth having a right triangle cross section in one example. The distance between the peaks and valleys of the sawtooth structure perpendicular to the substrate plane was determined by H=P sin($\theta$)cos($\theta$) where $\theta$ was the angle between the faces of dimension X and the plane of the substrate surface.

In one embodiment, on the top surface of the glass substrate, spatially distinct areas with different optical coatings were used, each of which corresponded to a different sensitivity to molecular attachment and thus, a different detectable analyte concentration range. Ligand arrays were formed partially on the different coated areas to take advantage of the different sensitivities to molecular attachment which expands the dynamic range of protein detection to five or more orders of magnitude.

Several prism films were made and tested; and the films had the following dimensions: Length: 25-30 mm; Width: 17-21 mm; Polymer thickness=0.17 mm; Substrate thickness=0.08 mm; Prism Pitches ranged from 40-120 microns; X had a range from 21-63 microns; and T glass=1 mm.

Test results were as follows.

In order to determine how the prism films affect the polarization of the light beam, height determinations were made of the slide standards with known height standards of silicon dioxide coatings on the surface. These measurements were compared to the case where a glass prism is used which is known to have very little birefringence and thus, has negligible effect on the light polarization that propagates through the system. The results show that the signal sensitivity of the prism films were 93%±5% of the glass prism case with a spot to spot variation of 3.3%±0.3%, comparable to the spot to spot variation seen in the glass prism case.

Figure 4:
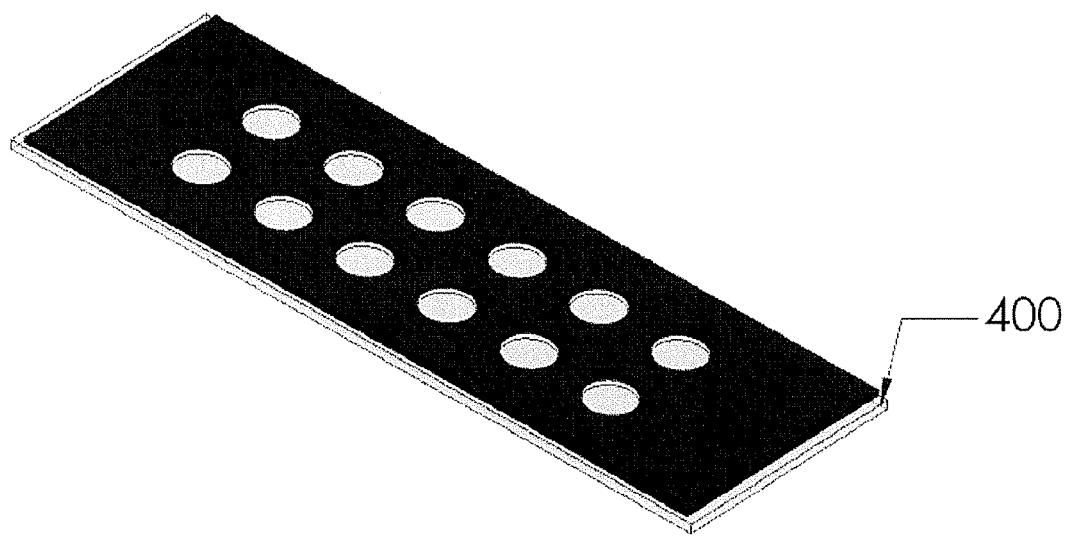
FIG. 4 is a projection view of a top member for forming a substrate of FIGS. 1 and 2 into a multiwell disposable.
Figure 4:

A substrate with a bottom surface configured as a sawtooth shaped prism in accordance with the present disclosure can be used to advantage in any system for determining the presence of an analyte in a sample so long as light is incident to the bottom surface of a substrate in a manner to obtain total internal reflection and an evanescent field in the plane of the top surface of the substrate. The substrate may comprise a single glass slide like a microscope slide 400 juxtaposed with a top member with a plurality of through holes to form an assembly as shown by member 400 in FIG. 4.

Figure 5:
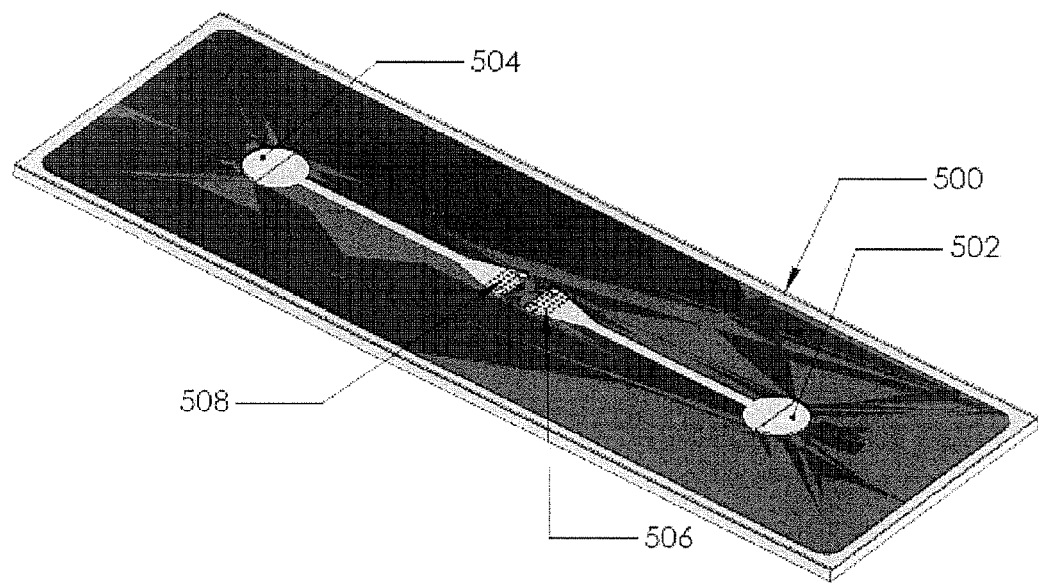
FIGS. 5 and 6 are projection views of alternative apparatus employing capillary action and a flow cell, respectively, to move a sample from an input position across an array of capture elements.
Figure 5:
Figure 6:
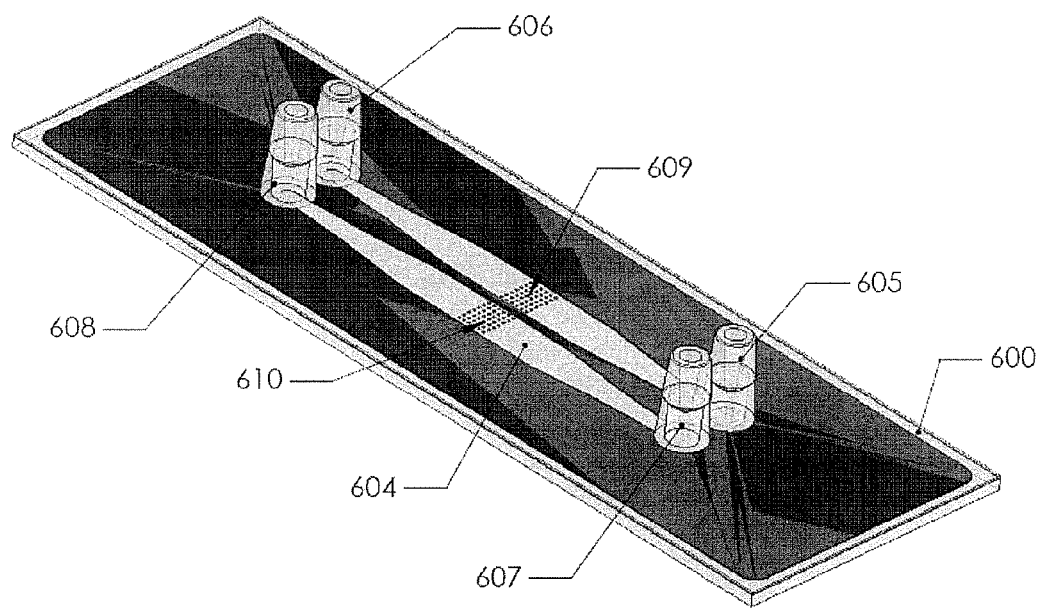
Figure 6:

FIGS. 5 and 6 show perspective views of alternative apparatus employing capillary action in the case of FIG. 5 and fluid pumps in the case of FIG. 6, to move a sample from an input position across an array of ligands. Specifically, FIG. 5 shows a substrate, typically a microscope slide 500 with first and second test positions for testing one of many possible liquids, such as blood serum samples. The samples are deposited at the half-circular openings 502 and 504 and move, by capillary action, to the associated triangular areas 506 and 508, respectively. An array of ligands is formed in each triangular area 506, 508, protected by a thin plastic film, and binding events between proteins in the array and analytes in a sample are imaged as described hereinbefore. The underside of slide 500 (not shown) is advantageously configured as a sawtooth prism in the areas beneath the triangular areas, allowing the light to be coupled into and out of the substrate in a manner to achieve total internal reflection about the top surface of the substrate while preserving the polarization state of the light beam upon entry and exit from the apparatus.

FIG. 6 shows a flow cell apparatus similar to that shown in FIG. 5. The apparatus comprises a substrate 600 with enclosed fluid channels 604 extending between an input port 605 and output port 606 and between an input port 607 and an output port 608. The apparatus of FIG. 6, one of many possible embodiments of a sample holder, is adapted for the use of a pipette to introduce a sample. The output ports are provided as air and liquid outlets to allow for a possible continuous flow of the sample through the flow cell apparatus. An introduced sample is moved by positive pressure to the associated microarrays 609 and 610 and beyond with the flow rate controlled. The underside of the substrate (not shown) again benefits from a sawtooth prism configuration in accordance with the principles of this invention in the areas under the microarrays. Binding events are imaged as disclosed hereinbefore.

The foregoing detailed description of embodiments of the present disclosure is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration those advancements, namely in accordance with the then current state of the art. It is intended that the scope of the invention be defined by the claims as written and equivalents as applicable. Reference to a claim element in the singular is not intended to mean "one and only one" unless explicitly so stated. Moreover, no element, component nor method or process step in this disclosure is intended to be dedicated to the public regardless of whether the element, component or step is explicitly recited in the claims. No claim element herein is to be construed under the provisions of 35 USC Sec. 112, sixth paragraph, unless the element is expressly recited using the phrase "means for . . ." and no method or process step herein is to be construed under those provisions unless the step, or steps, are expressly recited using the phrase "step(s) for . . .".

What is claimed is:

1. An apparatus for determining the presence of analytes in a sample, the apparatus comprising:
a transparent substrate with top and bottom surfaces spaced apart a distance d and formed of a material having an index of refraction n, wherein the substrate bottom surface includes a sawtooth prism having a cross-sectional sawtooth configuration comprising a light input portion and a light output portion which are mirror images of each other about a center line of the sample, and wherein the sawtooth prism has a height H, a pitch P, and an angle $\theta$ between an entry face and the plane of the substrate top surface according to the equation $H = P \sin \theta \cos \theta$.

2. The apparatus as in claim 1, wherein the substrate comprises a microscope slide.

3. The apparatus as in claim 1, further comprising an array of capture elements immobilized on the substrate top surface.

4. The apparatus as in claim 3, further comprising a plurality of arrays in spaced apart positions on the top surface of the substrate.

5. The apparatus as in claim 3, further comprising first and second coatings relating to different sensitivities to molecular attachment and wherein the array partially overlaps each of the coatings.

6. The apparatus as in claim 3, further comprising a fluid channel in communication with the array and a sample input port connected to the channel, the channel being dimensioned to move a sample by capillary action across the array.

7. The apparatus as in claim 1, further comprising a well-forming member integral with the substrate top surface, the member having a plurality of holes therein for forming sample wells, each of the wells in registry with an array.

8. The apparatus as in claim 5, further comprising a well forming member integral with the substrate top surface, the member having a plurality of holes therein for forming sample wells, each of the wells in registry with the array.

9. The apparatus as in claim 7, further comprising an optical system for directing light at an input face of at least one tooth of the sawtooth prism in a manner to obtain total internal reflection and an evanescent field in the plane of the top surface.

10. The apparatus as in claim 9, further comprising an imaging system for imaging the pattern of light reflected from the array and for determining patterns of changes from an initial stored light pattern.

11. The apparatus as in claim 1, wherein P >40 microns.

12. The apparatus as in claim 1, wherein the cross-sectional sawtooth configuration further comprises in each tooth two sides of unequal lengths, and wherein $X = P \cos \theta$ where X is the length of the shorter one of the two sides of the cross-sectional sawtooth configuration.

13. The apparatus as in claim 12, wherein the substrate comprises glass at least 1 mm thick and the sawtooth prism comprises a film of two layers, including a COC planar film and a UV-cured acrylic ester.

14. The apparatus as in claim 5, wherein the first and second coatings are taken from a group consisting of silicon dioxide, magnesium fluoride, tantalum pentoxide, titanium dioxide, and other metal oxides.

15. The apparatus as in claim 1, wherein the sawtooth prism comprises a separate film attached to the substrate bottom surface.

16. An apparatus comprising:
a substrate having a top surface for placement of a sample and a bottom surface, wherein the bottom surface has a consecutive tooth-shaped geometry with teeth arranged in rows and columns, with consecutive teeth in a column abutting one another to form a sawtooth configuration comprising a light input portion and a light output portion which are mirror images of each other about a center line of the sample and with adjacent teeth in a row being in alignment with one another.

17. The apparatus as in claim 16, further comprising a well-defining member with an array of apertures there through attached to the top surface of the substrate to define an array of wells.

18. The apparatus as in claim 17, wherein adjacent teeth in a row form an elongated wedge.

19. The apparatus as in claim 18, wherein consecutive wedges comprise adjacent faces non-parallel to the plane of the top surface and form a continuous sawtooth configuration.

20. The apparatus as in claim 16, wherein the bottom surface has a sawtooth geometry formed by an attached thin film with an embossed or preformed sawtooth geometry.

21. The apparatus as in claim 16, further comprising a source of light of wavelength $\lambda$ directed at an entrance face of at least one tooth of a sawtooth geometry wherein the area of the entrance face, X, is at least $$\frac{\lambda}{\sin\varphi}$$

where $\varphi$ is a divergence half-angle of the incident beam.

22. The apparatus as in claim 21, wherein a divergence of light due to diffraction in the substrate is less than or equal to 0.5°, and the pitch P from tooth to tooth is $P \geq 100\mu m \sin\theta \tan\theta$, where $\theta$ is the angle of incidence of the incoming light with respect to the plane of the top surface.

23. The apparatus as in claim 17, further comprising an array of capture elements in each well.

24. The apparatus as in claim 17, further comprising first and second coatings in each well wherein the coatings are selected to correspond to different levels of molecular attachment.

25. The apparatus as in claim 24, wherein the capture elements in each well partially overlap each of the first and second coatings corresponding to different levels of molecular attachment.

* * * * *